United States Patent
Augustine

(10) Patent No.: US 7,811,968 B2
(45) Date of Patent: Oct. 12, 2010

(54) PREPARATION OF PALLADIUM-GOLD CATALYSTS

(75) Inventor: Steven M. Augustine, Ellicott City, MD (US)

(73) Assignee: Lyondell Chemical Technology, L.P., Greenville, DE (US)

(*) Notice: Subject to any disclaimer, the term of this patent is extended or adjusted under 35 U.S.C. 154(b) by 613 days.

(21) Appl. No.: 11/801,935

(22) Filed: May 11, 2007

(65) Prior Publication Data

US 2008/0281122 A1 Nov. 13, 2008

(51) Int. Cl.
*B01J 23/00* (2006.01)
*B01J 23/02* (2006.01)
*B01J 23/04* (2006.01)
*B01J 23/42* (2006.01)
*B01J 23/44* (2006.01)
*B01J 23/58* (2006.01)
*B01J 23/70* (2006.01)
*B01J 23/72* (2006.01)
*B01J 21/04* (2006.01)

(52) U.S. Cl. ............ 502/330; 502/331; 502/339; 502/344; 502/345; 502/350; 502/439

(58) Field of Classification Search ............ 502/330, 502/331, 339, 344, 345, 350, 439
See application file for complete search history.

(56) References Cited

U.S. PATENT DOCUMENTS

| | | | | |
|---|---|---|---|---|
| 3,380,934 A | * | 4/1968 | Batzold | 502/339 |
| 3,743,607 A | | 7/1973 | Sennewald et al. | 252/430 |
| 3,775,342 A | | 11/1973 | Kronig et al. | 252/430 |
| 6,022,823 A | | 2/2000 | Augustine et al. | 502/243 |
| 6,207,128 B1 | * | 3/2001 | Sellin et al. | 423/588 |
| 6,358,882 B1 | * | 3/2002 | Salem et al. | 502/305 |
| 6,524,991 B2 | * | 2/2003 | Bowman et al. | 502/242 |
| 6,797,669 B2 | * | 9/2004 | Zhang et al. | 502/339 |
| 6,821,922 B1 | | 11/2004 | Tacke et al. | |
| 6,849,243 B1 | | 2/2005 | Hagemeyer et al. | |
| 7,521,393 B2 | * | 4/2009 | Blankenship et al. | 502/330 |
| 7,541,012 B2 | * | 6/2009 | Yeung et al. | 423/245.1 |
| 2001/0049335 A1 | * | 12/2001 | Kitchen et al. | 502/305 |
| 2006/0171877 A1 | * | 8/2006 | Dadachov | 423/610 |
| 2010/0099552 A1 | * | 4/2010 | Fu et al. | 502/209 |

* cited by examiner

*Primary Examiner*—Cam N Nguyen
(74) *Attorney, Agent, or Firm*—Shao-Hua Guo

(57) ABSTRACT

A method for preparing supported palladium-gold catalysts is disclosed. The method comprises increasing the porosity of a titanium dioxide support, impregnating the support with a palladium salt, a gold salt, and an optional alkali metal or ammonium compound, and reducing the calcined support. The resultant supported palladium-gold catalysts have increased activity in the acetoxylation.

17 Claims, No Drawings

PREPARATION OF PALLADIUM-GOLD CATALYSTS

FIELD OF THE INVENTION

The invention relates to supported palladium-gold catalysts. More particularly, the invention relates to supported palladium-gold catalysts that have increased catalytic activity and activity stability in acetoxylation.

BACKGROUND OF THE INVENTION

Palladium-gold catalysts are known. They are used in acetoxylation. For instance, the oxidation of ethylene in the presence of a palladium-gold catalyst and acetic acid produces vinyl acetate, which is a useful monomer for the polymer industry.

Acetoxylation is commonly performed by a vapor phase reaction using supported palladium-gold catalyst. Methods for supporting palladium-gold catalysts are also known. In general, the methods involve depositing a mixture of palladium and gold salts onto a support and then reducing the palladium and gold to metals.

Palladium and gold are both expensive precious metals. Therefore, many efforts have been made to increase the catalytic activity and reduce the amount of catalyst needed. For example, U.S. Pat. No. 6,022,823 teaches calcining the support impregnated with palladium and gold salts prior to reducing the metals. The catalyst shows improved activity.

Thus, it is still important to the chemical industry to find better ways to increase the catalytic activity of the supported palladium-gold catalysts. Ideally, the catalyst will have increased activity and require less precious metal.

SUMMARY OF THE INVENTION

The invention is a method for preparing a supported palladium-gold catalyst. The method comprises increasing the total porosity of a titanium dioxide (titania) support. The porosity of the titania support can be increased, for example, by mixing two titania supports which have different particle sizes. The titania support is then impregnated with a palladium salt, a gold salt, and optionally, with an alkali metal or ammonium compound. The impregnated support is then reduced to form a supported palladium-gold catalyst. Alternatively, the impregnated support is first calcined and then reduced to form the supported palladium-gold catalyst.

The invention includes the palladium-gold catalyst prepared according to the method of the invention and its use in acetoxylation for preparing vinyl acetate and allyl acetate. Compared to the palladium-gold catalysts known in the art, the catalysts prepared according to the method of the invention show improved catalytic activity in acetoxylation.

DETAILED DESCRIPTION OF THE INVENTION

The method of the invention comprises increasing the porosity of a titanium dioxide (titania) support. The support porosity can be measured by the total mercury intrusion. For instance, it can be measured using a Micromeretics AutoPore IV 9500 with triply distilled mercury. Samples are evacuated to 0.05 torr for 5 minutes, and intrusion is measured from 0.5 to 30,000 psia using 30 seconds equilibration times. Any method that increases the porosity of titania can be used. In one method, the titania support porosity is increased by mixing two titanias which have different sizes. In another method, the titania support porosity is increased by mixing a sintered titania with a non-sintered titania. In still a method, the titania support porosity is increased by mixing a spray-dried titania with a non-spray-dried titania.

Preferably, the titania support produced by the method of the invention has a porosity of greater than or equal to 0.31 mL Hg/g. More preferably, the titania support has a porosity of greater than or equal to 0.35 mL Hg/g. Most preferably, the titania support has a porosity of greater than or equal to 0.40 mL Hg/g.

Optionally, the titania support is calcined. The calcination is performed by heating the titania at a temperature preferably within the range of 500° C. to 900° C., more preferably 600° C. to 800° C., and most preferably 650° C. to 750° C.

The calcined or non-calcined support is impregnated with a palladium salt, a gold salt, and an optional alkali metal or ammonium compound. Any suitable impregnation methods can be used. For instance, U.S. Pat. No. 6,022,823, the teachings of which are incorporated herein by reference, teaches how to impregnate the support. For instance, the support can be simultaneously or successively treated with a palladium salt, a gold salt, and an alkali metal or ammonium compound. Preferably, the impregnation is performed in aqueous solution. The concentration of the solutions and the amount of each solution used is governed by the concentration of palladium and gold desired in the final catalyst product.

Suitable palladium salts include palladium chloride, sodium chloropalladite, palladium nitrate, palladium sulfate, the like, and mixtures thereof. Suitable gold salts include auric chloride, tetrachloroauric acid, sodium tetrachloroaurate, the like, and mixtures thereof. Sodium tetrachloroaurate and palladium chloride or sodium chloropalladite are most commonly used.

Suitable alkali metal or ammonium compounds include alkali metal or ammonium hydroxides, alkali metal or ammonium carbonates, alkali metal or ammonium bicarbonates, alkali metal or ammonium metasilicates, the like, and mixtures thereof.

One method to impregnate the support involves first treating the support with an aqueous solution of an alkali metal or ammonium compound. The treated support is then contacted with an aqueous solution containing palladium and gold salts.

In another method, the impregnation with the palladium and gold solutions is carried out before treatment with the aqueous solution of the alkali metal or ammonium compound. In this procedure, the absorptive capacity of the support is essentially completely filled with the aqueous solution of palladium and gold salts. Typically, this is accomplished by dropping the solution onto the support until incipient wetness is achieved. The support impregnated with the palladium and gold salts is then contacted with the alkali metal or ammonium compound.

A third method involves mixing the alkali or ammonium compound and precious metal compounds prior to coming into contact with the support. The contact with the support can be done by dropping or spraying the mixture onto the support until incipient wetness or by making a slurry of powdered support in the solution.

The impregnated catalyst is preferably washed with water to remove alkali metal salts such as chlorides formed during the impregnation and dried prior to calcination.

The impregnated support is reduced. Optionally, prior to the reduction, the impregnated support is calcined, i.e., heated at an elevated temperature in a non-reducing atmosphere. Preferably, the calcination is performed under such a condition that a portion of the palladium and gold salts are decomposed. More preferably, at least 10% of the palladium and gold salts are decomposed during the calcination.

Preferably, the calcination of the impregnated support is carried out at a temperature within the range of about 100° C. to about 600° C. More preferably, the temperature is within the range of 100° C. to 300° C. Most preferably, the temperature is within the range of 150° C. to 250° C.

Suitable non-reducing gases used for the calcination include inert or oxidizing gases such as helium, nitrogen, argon, neon, nitrogen oxides, oxygen, air, carbon dioxide, the like, and mixtures thereof. Preferably, the calcination is carried out in an atmosphere of nitrogen, oxygen, air or mixtures thereof.

The degree of decomposition of the palladium and gold salts depends on the calcination temperature, the deposited salt, and the length of time the impregnated support is calcined; it can be followed by monitoring volatile decomposition products. For example, when the support is impregnated with palladium and gold carbonates, the amount of carbon dioxide ($CO_2$) evolved can be measured.

Following the optional calcination step, the resulting product is reduced to convert the palladium and gold salts to the corresponding metals. The reduction is performed by heating in the presence of a reducing agent. Suitable reducing agents include ammonia, carbon monoxide, hydrogen, hydrocarbons, olefins, aldehydes, alcohols, hydrazine, primary amines, carboxylic acids, carboxylic acid salts, carboxylic acid esters, the like, and mixtures thereof. Hydrogen, ethylene, propylene, alkaline hydrazine and alkaline formaldehyde are preferred reducing agents and ethylene and hydrogen are particularly preferred.

Temperatures employed for the reduction can range from ambient up to about 600° C. Preferably, the reduction temperature is within the range of 300° C. to 600° C. Most preferably, the reduction temperature is within the range of 450° C. to 550° C. The reduction results in a supported palladium-gold catalyst.

The invention includes the supported palladium-gold catalyst made according to the method of the invention. Preferably, the supported palladium-gold catalyst comprises 0.1 wt % to 3 wt % of palladium, 0.1 wt % to 3 wt % of gold, and the weight ratio of palladium to gold is within the range of 5/1 to 1/3. More preferably, the supported palladium-gold catalyst comprises 0.5 wt % to 1.5 wt % of palladium and 0.25 wt % to 0.75 wt % of gold; the weight ratio of palladium to gold is within the range of 2.5/1 to 1/1.5.

The supported palladium-gold catalysts made according to the invention have many uses. They can be used, for example, in partial oxidation, hydrogenation, carbonylation, ammonia synthesis, selective hydrogenation, acetyloxylation, catalytic combustion or complete oxidation, three way catalysis, NOx removal, methanol synthesis, hydrogen peroxide synthesis, hydroformylation, alkylation and alkyl transfer, oxidative carbonylation, coupling of olefins with aromatics, and in the preparation of methyl isobutyl ketone from acetone.

The supported palladium-gold catalysts made according to the invention are particularly useful for the productions of vinyl acetate and allyl acetate. Various processes for producing vinyl acetate and allyl acetate are known. For instance, U.S. Pat. Nos. 3,743,607 and 3,775,342, the teachings of which are herein incorporated by reference, teach how to prepare vinyl acetate using palladium-gold catalysts.

For use in producing vinyl acetate and allyl acetate, the supported palladium-gold catalyst is preferably treated with a potassium compound such as potassium acetate. The potassium treatment can be done by mixing the catalyst with a potassium acetate solution, filtering, and drying the treated catalyst.

In general, vinyl acetate can be made by the oxidation of ethylene in the presence of acetic acid and the supported palladium-gold catalyst. Allyl acetate can be made by a similar manner but using propylene rather than ethylene.

I surprisingly found that the catalysts made according to the invention give not only high catalytic activity but also high activity stability. One problem in the existing prior art palladium-gold catalysts is that the catalysts lose activity with time. This invention provides a solution to that problem. The catalytic activity can be measured, for example, by the oxygen yield to vinyl acetate. The catalysts made according to the invention preferably has an oxygen yield to vinyl acetate greater than or equal to 35%, more preferably greater than or equal to 37%, and most preferably greater than or equal to 40% measured at 100 hours time on stream.

The following examples merely illustrate the invention. Those skilled in the art will recognize many variations that are within the spirit of the invention and scope of the claims.

Extrudate Preparation

A dry mixture is prepared by mixing 400 g titania powder (Millennium Chemicals DT51) with 8.2 g of binder which is specified in each of the following Examples, 5.5 g of plasticizer (polyethylene oxide), 217 g of water and 16 g of concentrated ammonium hydroxide are then added with gentle mixing forming a loose, dry mixture. Component amounts used both in gravimetric measurements and relative values are listed in Table 1. This mixture is then added to a Thermo Haake Rheomix 3000 mixer (625 ml internal volume) and mixed using sigma shaped blades. The blades are turned in a counter-rotating fashion at 50 rotations per minute (rpm) by a Thermo Haake Rheocord 300p drive unit over a 30 minute period to produce a well mixed paste from the initial components.

TABLE 1

PASTE COMPOSITION

| Component | Mass, g | Relative Amount, wt % |
|---|---|---|
| Titania Powder | 400 | 61.9 |
| Water | 217 | 33.6 |
| Plasticizer | 5.5 | 0.9 |
| Binder | 8.2 | 1.3 |
| Concentrated Ammonium Hydroxide | 16 | 2.5 |

The paste is removed from the mixing bowl and aged in a sealed plastic bag for 24 hrs to allow the paste to homogenize and the binder to fully hydrate. The paste is then extruded into ⅛" cylinders using a Thermo Haake Rheomex 202p with a Rheocord 300p drive unit. The extrudates are dried at room temperature for at least 24 hrs, and then at 105° C. for at least 16 hrs. The extrudates are calcined at 700° C. using the temperature ramp of 1° C./min from room temperature to 500° C., held at 500° C. for 1 hr and then ramped from 500° C. to 700° C. at 10° C./min and held at 700° C. for 6 hrs.

Mercury Porosimetry

Support porosity is measured using a Micromeretics AutoPore IV 9500 with triply distilled mercury. Samples are evacuated to 0.05 torr for 5 minutes, and intrusion is measured from 0.5 to 30,000 psia using 30 s equilibration times. Total cumulative intrusion is reported in Table 2.

Catalyst Preparation

NaAuCl4 (0.987 gram), Na2PdCl4 (2.645 gram), and NaHCO3 (2.760 grams) are dissolved in water (33 ml). The solution is applied to titania extrudates (100 grams) using a disposable pipette while tumbling the extrudates in a rotating dish until all the available extrudate pore volume is filled. The extrudates are then allowed to tumble for 30 minutes and then surface dried at 80-85° C. for 1 hour using a hot air gun. The mixture is dried in an oven at 105° C. for at least 16 hours and then extensively washed with deionized water to remove chlorides.

The above impregnated titania is calcined in a reactor at 200° C. in flowing air at 70 psig for three hours to affect a partial decomposition in excess of 10% of the deposited precious metal salts.

After the above calcination, the reactor is purged with nitrogen, and then a mixture of 20% hydrogen in nitrogen at 70 psig is introduced into the vessel. The temperature is ramped to 500° C. at a rate of 10° C./min. The temperature is held at 500° C. for three hours. The reactor is purged with nitrogen and the resultant catalyst is cooled to room temperature in flowing nitrogen.

25 grams of the resultant catalyst is contacted with an excess (>50 ml) aqueous solution of 5 w % potassium acetate and 0.5% potassium hydroxide at room temperature for 10 minutes. The mixture is decanted, and the potassium treated catalyst is dried at 105° C. in an oven for at least 4 hours.

Catalyst Testing

The catalyst is evaluated for vinyl acetate production using a packed bed plug flow tubular (nominal 1 inch O.D. stainless steel) reactor. The bed volume is 30 ml, and the catalyst is diluted with inert alumina in a ratio of 2.5:1 alumina to catalyst extrudates. The reactor pressure is 80 psig and the space velocity relative to catalyst employed is 3,800/hr at 0° C. and 1 atm of pressure with a composition of 84.7% ethylene, 9.9% acetic acid, 3.8% oxygen, and 1.6% nitrogen. The reactor coolant temperature is 130° C. The oxygen yield to vinyl acetate is reported in Table 2.

COMPARATIVE EXAMPLES 1-3

Comparative Examples 1-3 use the conventional methods of supported palladium-gold catalyst preparation. The titania supports used in these Comparative Examples have relatively small porosity as measured by mercury intrusion volume.

COMPARATIVE EXAMPLE 1

Sodium carboxymethylcellulose is used as the binder. The extrudates and catalyst are prepared as described above. The resulting porosity as measured by mercury intrusion and the catalyst performance as measured by the oxygen yield to vinyl acetate at 100 hrs time on stream are listed in Table 2.

COMPARATIVE EXAMPLE 2

Carboxymethylcellulose is used as the binder. The extrudates and catalyst are prepared as described above. The resulting porosity as measured by mercury intrusion and the catalyst performance as measured by the oxygen yield to vinyl acetate at 100 hrs time on stream are listed in Table 2.

COMPARATIVE EXAMPLE 3

Methylcellulose is used as the binder. The extrudates and catalyst are prepared as described above. The resulting porosity as measured by mercury intrusion and the catalyst performance as measured by the oxygen yield to vinyl acetate at 100 hrs time on stream are listed in Table 2.

EXAMPLES 4-8

Examples 4-8 illustrate the invention. In these Examples, various ways are used to increase the porosity of the support. The supported palladium-gold catalysts prepared have increased porosity and show increased performance as measured by the oxygen yield to vinyl acetate.

EXAMPLE 4

Carboxymethylcellulose is used as the binder. The extrudates and catalyst are prepared as described above with the exception that 300 g of DT51 ultrafine titania is replaced with 400 g of pigment grade titania (AT1 from Millennium Chemicals). The total amount of water used is also reduced from 217 g to 166 g. Comparison of Example 4 with Comparative Example 2 shows that the use of pigment grade titania increases total pore volume as measured by the total mercury intrusion. The palladium-gold catalyst supported on the support shows improved performance as measured by the oxygen yield to vinyl acetate at 100 hrs time on stream.

EXAMPLE 5

Methylcellulose is used as the binder. The extrudates and catalyst are prepared as described above with the exception that 10 g of the 400 g total titania powder is replaced by titania powder that has been sintered at 850° C. for 6 hrs. The total amount of water used is also reduced from 217 g to 160 g. Table 2 shows that the use of pre-sintered titania increases the total pore volume as measured by the total mercury intrusion. The palladium-gold catalyst supported on the support shows improved performance as measured by the oxygen yield to vinyl acetate at 100 hrs time on stream.

EXAMPLE 6

The extrudates and catalyst are prepared as described above with the exception that the 100 g of the 400 g total titania powder is replaced by titania powder that has been sintered at 900° C. for 6 hrs. Table 2 shows that the use of pre-sintered titania increases the total pore volume as measured by the total mercury intrusion. The palladium-gold catalyst supported on the support shows improved performance as measured by the oxygen yield to vinyl acetate at 100 hrs time on stream.

EXAMPLE 7

Carboxymethylcellulose is used as the binder. The extrudates and catalyst are prepared as described above with the exception that 100 g of the 400 g total titania powder is replaced by titania powder that is spray-dried. Titania slurry in water is spray-dried in a 3 ft diameter spray dryer. The inlet temperature is 220° C., the outlet temperature is 90° C., and the rotation speed is 27,000 rpm. The fraction collected at the cyclone having a particle size of 10-20 microns is used. The total amount of water used is also reduced from 217 g to 183 g. Table 2 shows that the use of the spray-dried titania increases the total pore volume as measured by the total mercury intrusion. The palladium-gold catalyst supported on the support shows improved performance as measured by the oxygen yield to vinyl acetate at 100 hrs time on stream.

EXAMPLE 8

The extrudates and catalyst are prepared as described above with the exception that the 100g of the 400 g total titania powder is replaced by titania powder that has been sintered at 825° C. for 6 hrs. Table 2 shows that the use of pre-sintered titania increases the total pore volume as measured by the total mercury intrusion. The palladium-gold catalyst supported on the support shows improved performance as measured by the oxygen yield to vinyl acetate at 100 hrs time on stream.

TABLE 2

MERCURY INTRUSION AND CATALYST PERFORMANCE

| Ex. No. | Total Mercury Intrusion Volume, ml/g | Catalyst Performance in VAM Production at 100 Hours, Oxygen Yield to Vinyl Acetate, % |
|---|---|---|
| C1 | 0.264 | 31.8 |
| C2 | 0.304 | 28.3 |
| C3 | 0.304 | 34.2 |
| 4 | 0.311 | 37.4 |
| 5 | 0.370 | 37.1 |
| 6 | 0.385 | 39.5 |
| 7 | 0.387 | 41.4 |
| 8 | 0.427 | 43.5 |

I claim:

1. A method for preparing a supported palladium-gold catalyst, said method comprising
   (a) increasing a titanium dioxide support intrusion volume to greater than or equal to 0.31 milliliter of mercury per gram by mixing two titanias which have different sizes, or by mixing a sintered titania with a non-sintered titania, or by mixing a spray-dried titania with a non-spray dried titania; impregnating the support with a palladium salt, gold salt, and an optional alkali metal or ammonium compound; and
   (b) reducing the impregnated support to form the supported palladium-gold catalyst.

2. The method of claim 1, wherein the titanium dioxide support has a total intrusion volume of greater than or equal to 0.35 milliliter per gram.

3. The method of claim 1, wherein the titanium dioxide support has a total intrusion volume of greater than or equal to 0.40 milliliter per gram.

4. The method of claim 1, wherein the alkali metal or ammonium compound in selected from the group consisting of hydroxides, carbonates, bicarbonates, metasilicates, and mixtures thereof.

5. The method of claim 1, wherein the alkali metal or ammonium compound is a carbonate or bicarbonate.

6. The method of claim 1, wherein the palladium salt is selected from the group consisting of palladium chloride, sodium chloropalladite, palladium nitrate, and palladium sulfate; and the gold salt is selected from the group consisting of auric chloride, tetrachloroauric acid, sodium tetrachloroaurate, and mixtures thereof 7. A method for preparing a supported palladium-gold catalyst, said method comprising
   (a) increasing a titanium dioxide support intrusion volume to greater than or equal to 0.31 milliliter of mercury per gram by mixing two titanias which have different sizes, or by mixing a sintered titania with a non-sintered titania, or by mixing a spray-dried titania with a non-spray dried titania; impregnating the support with a palladium salt, gold salt, and an alkali metal or ammonium compound;
   (b) calcining the impregnated support; and
   (c) reducing the calcined support to form the supported palladium-gold catalyst.

8. The method of claim 7, wherein the calcination is performed in a non-reducing atmosphere at a temperature within the range of 100° C. to 600° C.

9. The method of claim 8, wherein the non-reducing atmosphere is selected from the group consisting of helium, nitrogen, argon, neon, nitrogen oxides, oxygen, air, carbon dioxide, and mixtures thereof.

10. The method of claim 9, wherein the calcination temperature is within the range of 100° C. to 300° C.

11. The method of claim 7, wherein the reduction is performed in the presence of hydrogen.

12. The method of claim 11, wherein the reduction is performed at a temperature within the range of 300° C. to 600° C.

13. The method of claim 11, wherein the reduction is performed at a temperature within the range of 450° C. to 550° C.

14. The method of claim 7, which farther comprises (d) treating the supported palladium-gold catalyst with a potassium salt.

15. A method for preparing a supported palladium-gold catalyst, said method comprising
   (a) increasing a titanium dioxide support intrusion volume to greater than or equal to 0.31 milliliter of mercury per gram by mixing two titanias which have different sizes, or by mixing a sintered titania with a non-sintered titania, or by mixing a spray-dried titania with a non-spray dried titania; calcining the titanium dioxide support;
   (b) impregnating the calcined support with a palladium salt, a gold salt, and an alkali metal or ammonium compound;
   (c) calcining the impregnated support; and
   (d) reducing the calcined support from step (c) to form the supported palladium-gold catalyst.

16. The method of claim 15, wherein the titanium dioxide support has a total intrusion volume of greater than or equal to 0.35 milliliter of mercury per gram.

17. The method of claim 15, wherein the titanium dioxide support has a total intrusion volume of greater than or equal to 0.40 milliliter of mercury per gram.

* * * * *